US012745984B2

(12) United States Patent
He et al.

(10) Patent No.: US 12,745,984 B2
(45) Date of Patent: Sep. 29, 2026

(54) TISSUE ELASTICITY MEASUREMENT METHOD AND DEVICE

(71) Applicant: WUXI HISKY MEDICAL TECHNOLOGIES CO., LTD., Wuxi (CN)

(72) Inventors: Qiong He, Jiangsu (CN); Jinhua Shao, Jiangsu (CN); Jin Sun, Jiangsu (CN); Houli Duan, Jiangsu (CN)

(73) Assignee: WUXI HISKY MEDICAL TECHNOLOGIES CO., LTD., Wuxi (CN)

( * ) Notice: Subject to any disclaimer, the term of this patent is extended or adjusted under 35 U.S.C. 154(b) by 224 days.

(21) Appl. No.: 17/754,143

(22) PCT Filed: Jul. 28, 2020

(86) PCT No.: PCT/CN2020/105028

§ 371 (c)(1),
(2) Date: Mar. 24, 2022

(87) PCT Pub. No.: WO2021/057238

PCT Pub. Date: Apr. 1, 2021

(65) Prior Publication Data

US 2022/0287683 A1 Sep. 15, 2022

(30) Foreign Application Priority Data

Sep. 26, 2019 (CN) ......................... 201910919079.0

(51) Int. Cl.
*A61B 8/00* (2006.01)
*A61B 8/08* (2006.01)

(52) U.S. Cl.
CPC ................ *A61B 8/485* (2013.01); *A61B 8/08* (2013.01); *A61B 8/4488* (2013.01); *A61B 8/5276* (2013.01); *A61B 8/54* (2013.01)

(58) Field of Classification Search
None
See application file for complete search history.

(56) References Cited

U.S. PATENT DOCUMENTS

2011/0237945 A1* 9/2011 Foroughi ............. A61B 8/4263 600/438
2011/0263978 A1* 10/2011 Chen ...................... A61B 8/485 600/438

(Continued)

FOREIGN PATENT DOCUMENTS

CA 2685886 A1 * 11/2008 ........... A61B 5/0051
CN 103040524 A 4/2013

(Continued)

OTHER PUBLICATIONS

English translation of WO 2011/034005 (Year: 2011).*

*Primary Examiner* — Katherine L Fernandez
(74) *Attorney, Agent, or Firm* — VLP Law Group, LLP

(57) ABSTRACT

Disclosed are a tissue elasticity measurement method and device. The method includes: transmitting a first ultrasonic signal to a tissue in a measurement area; tracking at least one imaging line of the first ultrasonic signal; determining, according to the imaging line at a plurality of time points, a motion state of each imaging line; and selecting a position with an imaging line with a motion state meeting a preset condition and performing tissue elasticity measurement. The problem of impact on the motion state of the issue in a to-be-measured area on the accuracy of elasticity measurement is solved, and accuracy of elasticity measurement on the tissue in the measurement area is improved.

3 Claims, 3 Drawing Sheets

(56) References Cited

U.S. PATENT DOCUMENTS

| | | | | |
|---|---|---|---|---|
| 2013/0028536 | A1 | 1/2013 | Hazard | |
| 2015/0148674 | A1* | 5/2015 | Park | A61B 8/4245 600/438 |
| 2017/0042511 | A1 | 2/2017 | Labyed et al. | |
| 2017/0196533 | A1* | 7/2017 | Labyed | A61B 8/5276 |
| 2017/0340310 | A1* | 11/2017 | Carlini | G01S 7/52022 |
| 2017/0347992 | A1 | 12/2017 | Anand | |
| 2020/0121294 | A1* | 4/2020 | Tsymbalenko | A61B 8/5246 |

FOREIGN PATENT DOCUMENTS

| | | | | |
|---|---|---|---|---|
| CN | 104688266 | A | 6/2015 | |
| CN | 106419961 | A | 2/2017 | |
| CN | 106510766 | A | 3/2017 | |
| CN | 110613484 | A | 12/2019 | |
| CN | 110613485 | A | 12/2019 | |
| EP | 2878270 | A2 | 6/2015 | |
| EP | 3320850 | A1 | 5/2018 | |
| FR | 3069150 | A1 | 1/2019 | |
| JP | 2009118798 | A | 6/2009 | |
| JP | 2014162966 | A | 9/2014 | |
| KR | 20150113925 | A | 10/2015 | |
| KR | 20170085516 | A | 7/2017 | |
| WO | WO-2011034005 | A1 * | 3/2011 | A61B 8/0858 |
| WO | 2018178379 | A1 | 10/2018 | |
| WO | 2019072552 | A1 | 4/2019 | |

* cited by examiner

TISSUE ELASTICITY MEASUREMENT METHOD AND DEVICE

CROSS-REFERENCE TO RELATED APPLICATIONS

This application is a National Stage of International Application No. PCT/CN2020/105028, filed on Jul. 28, 2020, which claims priority to Chinese Patent Application No. 201910919079.0, filed on Sep. 26, 2019, both of which are hereby incorporated by reference in their entireties.

TECHNICAL FIELD

This application relates to the technical field of medical imaging, and in particular to a tissue elasticity measurement method and device.

BACKGROUND

Various chronic diseases, such as viral hepatitis (the hepatitis A, the hepatitis B, the hepatitis C, and the like), are accompanied during development thereof by fibrosis of damaged tissue, and the process of tissue fibrosis may be accompanied by changes in tissue elasticity. Therefore, tissue elasticity information is a parameter that may be used to diagnose a degree of tissue fibrosis.

Transient Elastography (TE) is a technique for quantitatively measuring tissue elastic modulus, which can comprehensively reflect the degree of tissue fibrosis by Liver Stiffness Measurement (LSM).

Transient Elastography, however, cannot acquire tissue structure information of a measurement area, especially two-dimensional structure information of the tissue. Typically, technicians can only set and arrange an ultrasound probe for transient elastography based on experience. As such, during tissue elasticity measurement, an ultrasonic probe measures a measurement area to generate an image. However, measurement errors tend to occur due to inevitable reasons, e.g. movements of tissue caused by breathing and heartbeat, etc., as well as influencing factors such as large blood vessels, cysts or ascites, etc., that may be included in a to-be-measured area. Thus, when selecting a measurement area, how to avoid the foregoing situations and select a measurement area that is less affected is an issue that needs consideration.

In the related arts, there is still a need for an effective solution to the problem of how to select a measurement area with less influence on tissue dynamics during tissue elasticity measurement.

SUMMARY

In view of the problem in the related art of how to select a measurement area with less influence on tissue dynamics during tissue elasticity measurement, the present invention provides a method and device for tissue elasticity measurement to solve at least the above problem.

According to an aspect of the present invention, there is provided a tissue elasticity measurement method, and the method includes:

transmitting a first ultrasonic signal to a tissue in a measurement area, tracking at least one imaging line of the first ultrasonic signal;

determining, according to the imaging line at a plurality of time points, a motion state of each imaging line; and selecting a position with an imaging line with a motion state meeting a preset condition and performing tissue elasticity measurement.

In an embodiment, the transmitting a first ultrasonic signal to a tissue in a measurement area includes:

performing ultrasonic scanning by controlling N ultrasonic array elements on an elasticity measurement probe to form at least one imaging line of the first ultrasonic signal, where N is a positive integer.

In an embodiment, the motion state is characterized by a plurality of motion parameters; and when the plurality of motion parameters meet corresponding preset conditions, it is determined that the motion state meets the preset condition.

In an embodiment, the tissue elasticity measurement includes: transmitting shear waves to the tissue in the measurement area; controlling M ultrasonic array elements on the probe to transmit a second ultrasonic signal at a selected position and collecting an echo signal of the second ultrasonic signal; and processing the echo signal of the second ultrasonic signal for tissue elasticity measurement, where M is a positive integer.

In an embodiment, the method further includes, before transmitting a first ultrasonic signal to a tissue in a measurement area:

controlling R ultrasonic array elements on the probe to transmit a third ultrasonic signal to the tissue in the measurement area and collecting an echo signal of the third ultrasonic signal, so as to determine a position of the measurement area, where R is a positive integer.

According to another aspect of the present invention, there is also provided a tissue elasticity measurement device, and the tissue elasticity measurement device includes a control host and an elasticity measurement probe;

the elasticity measurement probe transmits a first ultrasonic signal to a tissue in a measurement area;

the control host tracks at least one imaging line of the first ultrasonic signal;

the control host determines, according to the imaging line at a plurality of time points, a motion state of each imaging line; and the control host selects a position with an imaging line with a motion state meeting a preset condition, and the elasticity measurement probe performs tissue elasticity measurement.

In an embodiment, the control host performs ultrasonic scanning by controlling N ultrasonic array elements on an elasticity measurement probe to form at least one imaging line of the first ultrasonic signal, where N is a positive integer.

In an embodiment, the motion state is characterized by a plurality of motion parameters, and when the plurality of motion parameters meet corresponding preset conditions, it is determined that the motion state meets the preset condition.

In an embodiment, the control host transmits shear waves to the tissue in the measurement area; the control host controls M ultrasonic array elements on the elasticity measurement probe to transmit a second ultrasonic signal at a selected position and to collect an echo signal of the second ultrasonic signal; and the echo signal of the second ultrasonic signal is processed, where M is a positive integer.

In an embodiment, before the elasticity measurement probe transmits a first ultrasonic signal to a tissue in a measurement area, the control host controls R ultrasonic array elements on the elasticity measurement probe to transmit a third ultrasonic signal to the tissue in the measurement area and to collect an echo signal of the third ultrasonic signal, so as to determine a position of the measurement area, where R is a positive integer.

By transmitting a first ultrasonic signal to a tissue in a measurement area; tracking at least one imaging line of the first ultrasonic signal; determining a motion state of each imaging line according to the imaging line at a plurality of time points; and selecting a position with an imaging line with a motion state meeting a preset condition and performing tissue elasticity measurement, the present invention solves the problem of impact on the motion state of the issue in an area to be measured on the accuracy of elasticity measurement and improves the accuracy of elasticity measurement on the tissue in the measurement area.

BRIEF DESCRIPTION OF DRAWINGS

The accompanying drawings described herein are used to provide further understanding of the present invention and constitute a part of this application. The illustrative embodiments of the present invention and descriptions thereof are used to explain the present invention, and do not constitute any improper limitation on the present invention. In the drawings.

DETAILED DESCRIPTION OF EMBODIMENTS

To clarify objectives, technical solutions, and advantages of this application, the following further describes this application in detail with reference to the accompanying drawings and embodiments. It should be understood that the specific embodiments described herein are used for illustration only, and are not intended for use as limiting of this application.

Figure 1:
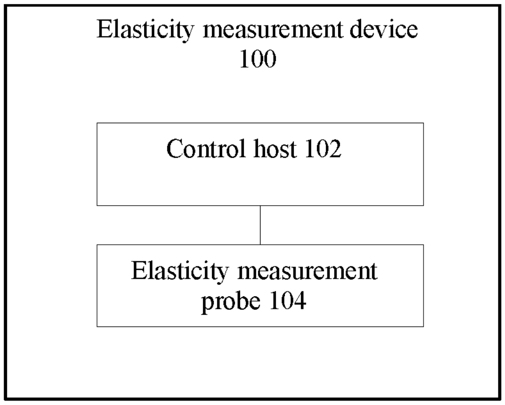
FIG. 1 is a structural block diagram 1 of a tissue elasticity measurement device according to an embodiment of the present invention.
Figure 2:
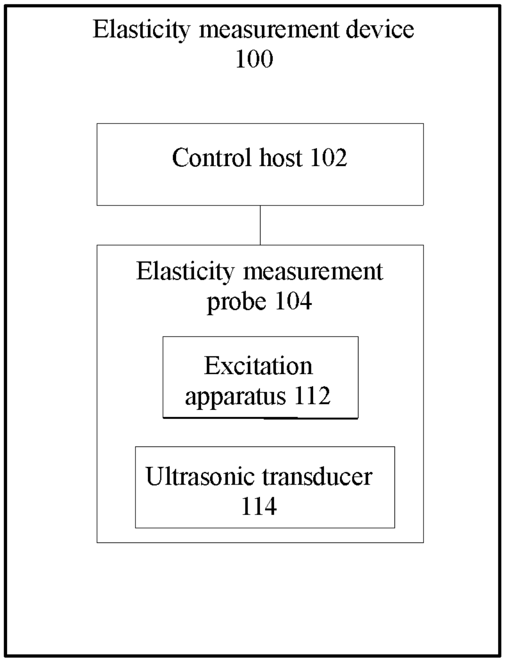
FIG. 2 is a structural block diagram 2 of a tissue elasticity measurement device according to an embodiment of the present invention.

In the embodiments of the present invention, FIG. 1 is a structural block diagram 1 of a tissue elasticity measurement device according to an embodiment of the present invention. As shown in FIG. 1, the tissue elasticity measurement device 100 includes a control host 102 and an elasticity measurement probe 104. FIG. 2 is a structural block diagram 2 of a tissue elasticity measurement device according to an embodiment of the present invention. As shown in FIG. 2, the elasticity measurement probe 104 includes an excitation apparatus 112 and an ultrasonic transducer 114. The excitation apparatus 112 and the ultrasonic transducer 114 may be integrated in the elastic measurement probe 104, and the control host 102 or the elastic measurement probe 104 transmits a control command to the excitation apparatus 112 and the ultrasonic transducer 114 to realize measurement of an area to be measured. The excitation apparatus 112 of a shear wave includes any of the following apparatuses: a vibrator, an ultrasonic transducer, and a loudspeaker.

An excitation process of the shear wave includes: the vibrator applies low-frequency instantaneous vibration on an outer surface of the tissue to generate shear waves in the tissue; ultrasonic waves emitted by the ultrasonic transducer 114 are focused inside the tissue to generate a sound radiation force, so as to generate shear waves inside the tissue; the loudspeaker generates sound waves of a specific frequency on the outer surface of the tissue to generate shear waves in the tissue.

It should be noted that, in the method of using the ultrasonic transducer 114 to generate shear waves, the ultrasonic transducer 114 for generating shear waves and the ultrasonic transducer 114 for transmitting ultrasonic waves and receiving ultrasonic echo signals may be the same one or two different ones.

The ultrasonic echo signal corresponding to each shear wave is received by using the ultrasonic transducer 114. The ultrasonic transducer 114 sends the received ultrasonic echo signal corresponding to each shear wave to the control host 102, so that the control host 102 performs subsequent processing on each ultrasonic echo signal.

A propagation characteristic parameter of each shear wave is obtained respectively according to the ultrasonic echo signal corresponding to each shear wave. According to these propagation characteristic parameters and a tissue density of the area to be measured, an elastic parameter of the area to be measured is obtained by calculation.

The elasticity measurement process includes:

The excitation apparatus 112 applies low-frequency instantaneous vibration on the outer surface of the tissue in the area to be measured, so as to generate shear waves in the tissue; then the ultrasonic transducer 114 transmits ultrasonic waves to the tissue and collects ultrasonic echoes, and the control host 102 performs elasticity calculation of the tissue according to collected ultrasonic echo signals.

Figure 3:
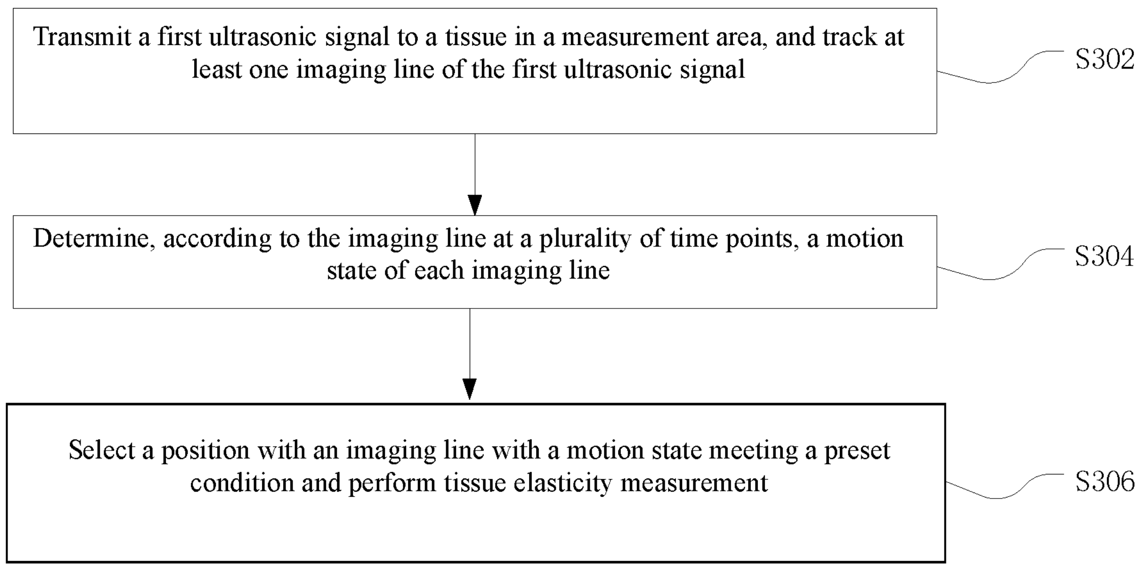
FIG. 3 is a flowchart 1 of a tissue elasticity measurement method according to an embodiment of the present invention.

In another embodiment of the present invention, FIG. 3 is a flowchart 1 of a tissue elasticity measurement method according to an embodiment of the present invention. As shown in FIG. 3, the method includes the following steps.

Step S302. Transmit a first ultrasonic signal to a tissue in a measurement area, and track at least one imaging line of the first ultrasonic signal.

Step S304. Determine, according to the imaging line at a plurality of time points, a motion state of each imaging line.

Step S306. Select a position with an imaging line with a motion state meeting a preset condition and perform tissue elasticity measurement.

In the present invention, by transmitting a first ultrasonic signal to a tissue in a measurement area; tracking at least one imaging line of the first ultrasonic signal; determining, according to the imaging line at a plurality of time points, a motion state of each imaging line; and selecting a position with an imaging line with a motion state meeting a preset condition, tissue elasticity measurement is performed. By automatically selecting one or more positions of imaging lines with motion states meeting the preset condition through one measurement of the foregoing first ultrasonic wave, to determine one or more measurement positions of the tissue elasticity measurement, the present invention solves the problem of impact of the motion state of the issue in an to-be-measured area on the accuracy of elasticity measurement, and improves the accuracy of elasticity measurement for the tissue in the measurement area.

In this embodiment, the elasticity measurement device 100 includes an elasticity measurement probe 104. In the case that the elasticity measurement probe 104 includes the ultrasonic transducer 114, a preset probe excitation area on the ultrasonic transducer 114 may be selected. The preset probe excitation area corresponds to N array element components, where N is a positive integer. The N array element components send the first ultrasonic signal through different grouping scanning methods to form the at least one imaging line, track measurement values of the at least one imaging line, and determine the motion parameter value at different positions of the tissue in the measurement area according to the motion parameter value of each imaging line. Since the ultrasonic transducer 114 may have a plurality of probe excitation areas on the elasticity measurement probe 104, the probe excitation areas may be selected through some experiments or computer simulations. That is, to select probe excitation areas with small interference between array elements and corresponding to the array element with higher measurement accuracy, thereby improving elasticity measurement accuracy of the shear waves.

In this embodiment, the elasticity measurement probe 104 obtains ultrasonic measurement data of the tissue in the measurement area, and the measurement data includes: tracking a measurement value of at least one imaging line of an ultrasonic wave, and determining the motion parameter value of the measurement area according to the measurement value at a plurality of time points. The motion state of the foregoing embodiment is characterized by the plurality of motion parameters, where the elasticity measurement probe 104 (two-dimensional imaging or three-dimensional imaging) selects a plurality of pieces of data of one or more imaging lines over time. Cross-correlation, optical flow, and other block matching methods, phase difference calculation or filtering, and other methods are used to calculate motion parameter values between two consecutive time points or several time points apart, it is possible to select a motion parameter value corresponding to the imaging line in the tissue in the measurement area, so as to track and determine the motion state of each imaging line. In the case that motion states of some imaging lines exceed the threshold range, shear wave measurement is not performed on the tissue in the measurement area corresponding to some imaging lines, and only when motion parameter values of motion states of some imaging lines are less than the preset threshold, the shear wave measurement is performed on the tissue in the measurement area corresponding to some imaging lines. Alternatively, in the case that the motion parameter values of the imaging lines of the tissue in the measurement area are all less than the preset threshold, it is determined that the tissue in the measurement area is the shear wave measurement position. In this embodiment, through one ultrasonic imaging line measurement on the foregoing elasticity measurement probe 104, one or more positions with an imaging line with a motion state meeting the preset condition are automatically selected to determine one or more measurement positions for tissue elasticity measurement. In the foregoing method of tracking the motion state of each imaging line independently, a range of the tissue in the measurement area in which shear wave measurement may be performed is selected; alternatively, the method may indicate that shear wave measurement cannot be performed on a part of areas of the tissue in the measurement area, and instruct testers to perform measurement on other areas of the tissue.

In this embodiment, a determination time of the motion state of the tissue in the measurement area may be after or before transmitting of shear waves by the elasticity measurement device 100. Here, after the elasticity measurement device 100 transmits shear waves to the tissue in the measurement area, the control host 102 may determine the tissue in the measurement area corresponding to the imaging line as the elasticity measurement position when the motion parameter value is smaller than the preset threshold. M ultrasonic array elements on the elasticity measurement probe 104 are controlled to transmit a second ultrasonic signal at a selected elasticity measurement position and to collect an echo signal of the second ultrasonic signal, and the echo signal of the second ultrasonic signal is processed for tissue elasticity measurement, where M is a positive integer. The control host 102 may also determine, before the elasticity measurement device 100 transmits shear waves to the tissue in the measurement area, the imaging line at a plurality of time points of the first ultrasonic wave, to determine a motion parameter value of each imaging line. In the case that the motion parameter value is less than the preset threshold, the elasticity measurement device 100 transmits shear waves to the tissue in the measurement area, controls M ultrasonic array elements on the elasticity measurement probe 104 to transmit a second ultrasonic signal at a selected elasticity measurement position and to collect an echo signal of the second ultrasonic signal, and processes the echo signal of the second ultrasonic signal for tissue elasticity measurement, where M is a positive integer.

Figure 4:
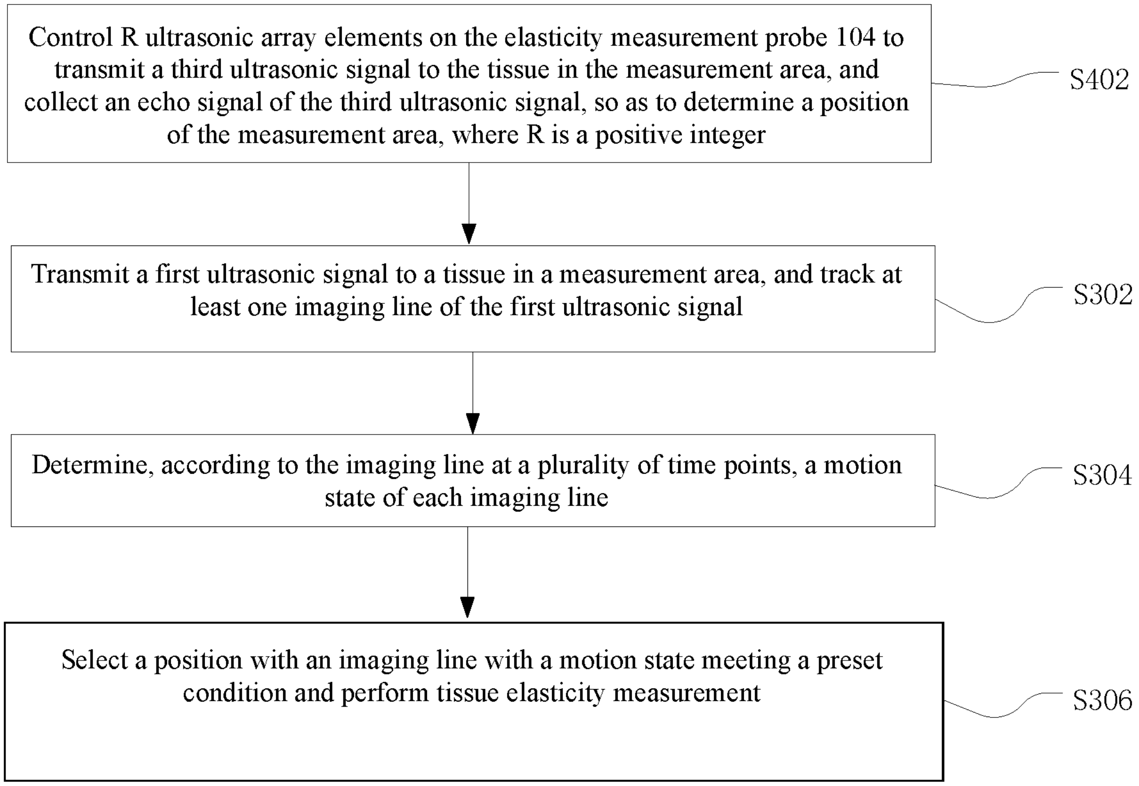
FIG. 4 is a flowchart 2 of a tissue elasticity measurement method according to an embodiment of the present invention.

In another embodiment of the present invention, FIG. 4 is a flowchart 2 of a tissue elasticity measurement method according to an embodiment of the present invention. As shown in FIG. 4, the method includes the following steps.

Step S402. Control R ultrasonic array elements on the elasticity measurement probe 104 to transmit a third ultrasonic signal to the tissue in the measurement area and to collect an echo signal of the third ultrasonic signal, so as to determine a position of the measurement area, where R is a positive integer.

Step S302. Transmit a first ultrasonic signal to a tissue in a measurement area, and track at least one imaging line of the first ultrasonic signal.

Step S304. Determine, according to the imaging line at a plurality of time points, a motion state of each imaging line.

Step S306. Select a position with an imaging line with a motion state meeting a preset condition and performing tissue elasticity measurement.

Through the foregoing steps, the elasticity measurement device 100 determines the position of the tissue in the measurement area by transmitting the third ultrasonic signal to the tissue in the measurement area and collecting the echo signal of the third ultrasonic signal, and instructs an inspector to select the measurement area. For example, in the case of measuring a liver area of the human body, the ultrasonic wave images an image inside the human body, avoiding the bone, the large blood vessel, the cyst, or the ascites area, and the inspector selects the liver area.

The implementation of the foregoing tissue elasticity measurement method in the foregoing elasticity measurement device 100 may include: the transmitting a first ultrasonic signal to a tissue in a measurement area includes:

- performing ultrasonic scanning by N ultrasonic array elements on an elasticity measurement probe 104 under the control of the control host 102 to form at least one imaging line of the first ultrasonic signal, where N is a positive integer; tracking a motion parameter value of the imaging line of the first ultrasonic signal; and obtaining, by the control host 103, the motion parameter value to determine the motion state of the tissue in the measurement area;
- determining, by the control host 102, whether the motion parameter value of the imaging line is less than the preset threshold; and
- in the case that the motion parameter value is less than the preset threshold, determining, by the control host 102, that the tissue in the measurement area corresponding to the imaging line is the position for elasticity measurement, and performing, by the elasticity measurement probe 104, elasticity measurement on the measurement area.

In an embodiment, a computer device is provided, including a memory and a processor, a computer program is stored in the memory, and the processor implements the foregoing steps of elasticity measurement when executing the computer program.

A person of ordinary skill in the art may understand that some or all processes of the implementation of the foregoing method in the embodiments may be implemented by instructing relevant hardware through a computer program. The computer program may be stored in a non-volatile computer-readable storage medium, and when the computer program is executed, the processes of the embodiments of the foregoing methods may be included. Any reference to a memory, storage, database, or other medium used in the embodiments provided in this application may include a non-volatile and/or volatile memory. The non-volatile memory may include a read only memory (ROM), a programmable ROM (PROM), an electrically programmable ROM (EPROM), an electrically erasable programmable ROM (EEPROM), or a flash memory. The volatile memory may include a random access memory (RAM) or an external cache memory. By way of illustration and not limitation, the RAM is available in various forms such as a static RAM (SRAM), a dynamic RAM (DRAM), a synchronous DRAM (SDRAM), a double data rate SDRAM (DDRSDRAM), an enhanced SDRAM (ESDRAM), a synchronization link (Synchlink) DRAM (SLDRAM), a Rambus (Rambus) direct RAM (RDRAM), a direct Rambus dynamic RAM (DRDRAM), and a Rambus dynamic RAM (RDRAM).

Various technical features of the foregoing embodiments may be combined arbitrarily. For the sake of brevity, not all possible combinations of the technical features in the foregoing embodiments are described. However, as long as there is no contradiction in the combination of these technical features, they shall be considered to be within the scope of this specification.

The foregoing embodiments only involve several implementations of this application, although descriptions thereof are specific and in details, they shall not be considered as any limitation to the scope of the inventive patent. Please note that various modifications and improvements might come to a person skilled in the art without departing from the concept of this application, which all fall within the protection scope of this application. Therefore, the protection scope of the patent of this application shall be subject to the appended claims.

The invention claimed is:

1. A tissue elasticity measurement device, wherein the tissue elasticity measurement device comprises a control host of medical imaging and an elasticity measurement probe;

the elasticity measurement probe is configured to transmit a first ultrasonic signal to a tissue in a measurement area, wherein the control host performs ultrasonic scanning by controlling N ultrasonic array elements on the elasticity measurement probe to form at least one imaging line of the first ultrasonic signal, wherein N is a positive integer;

the control host is configured to track a measurement value of the at least one imaging line of the first ultrasonic signal;

the control host is further configured to determine, according to the at least one imaging line at a plurality of time points, a motion state of each imaging line of the at least one imaging line, wherein the motion state is characterized by a plurality of motion parameters, the control host determines values of the plurality of motion parameters of each imaging line of the at least one imaging line according to the measurement value at the plurality of time points, when the values of the motion parameters meet a corresponding preset condition, it is determined that the motion state meets the preset condition; and the control host is further configured to select a position of the at least one imaging line with the motion state meeting the preset condition to determine one or more measurement positions of tissue elasticity measurement, the elasticity measurement probe is further configured to perform the tissue elasticity measurement at the one or more measurement positions, and an elastic parameter is obtained to diagnose a degree of tissue fibrosis.

2. The device of claim 1, wherein the control host is further configured to transmit shear waves to the tissue in the measurement area;

the control host is further configured to control M ultrasonic array elements on the elasticity measurement probe to transmit a second ultrasonic signal at a selected position and to collect an echo signal of the second ultrasonic signal; and the echo signal of the second ultrasonic signal is processed, wherein Mis a positive integer.

3. The device of claim 1, wherein before the elasticity measurement probe transmits the first ultrasonic signal to the tissue in the measurement area, the control host is further configured to control R ultrasonic array elements on the elasticity measurement probe to transmit a third ultrasonic signal to the tissue in the measurement area and to collect an echo signal of the third ultrasonic signal, so as to determine a position of the measurement area, wherein R is a positive integer.

* * * * *